US00RE36606E

United States Patent [19]

Chriki

[11] E Patent Number: Re. 36,606

[45] Reissued Date of Patent: Mar. 7, 2000

[54] SYNERGISTIC PHARMACEUTICAL COMPOSITIONS

[75] Inventor: Georges Chriki, Jerusalem, Israel

[73] Assignee: Massa Technology S.A., Luxembourg, Luxembourg

[21] Appl. No.: 09/168,317

[22] Filed: Oct. 7, 1998

Related U.S. Patent Documents

Reissue of:

[64] Patent No.: 5,707,981
Issued: Jan. 13, 1998
Appl. No.: 08/469,371
Filed: Jun. 6, 1995

U.S. Applications:

[63] Continuation-in-part of application No. 08/281,642, Jul. 28, 1994, abandoned.

[51] Int. Cl.[7] ..... A61K 31/56; A61K 3/58

[52] U.S. Cl. ..... 514/170; 514/174

[58] Field of Search ..... 514/170, 174

[56] References Cited

U.S. PATENT DOCUMENTS

| | | | |
|---|---|---|---|
| 2,990,401 | 6/1961 | Bernstein et al. | 540/63 |
| 3,035,050 | 5/1962 | Hydorn | 540/63 |
| 3,892,857 | 7/1975 | Difazio et al. | 514/174 |
| 3,899,581 | 8/1975 | Agusti | 514/174 |
| 3,934,013 | 1/1976 | Poulsen | 514/170 |
| 4,107,161 | 8/1978 | Agusti | 540/70 |
| 4,233,295 | 11/1980 | Hill et al. | 424/238 |

FOREIGN PATENT DOCUMENTS

| | | |
|---|---|---|
| 020117 | 5/1980 | European Pat. Off. . |
| 0196121 | 2/1986 | European Pat. Off. . |
| 173478 | 3/1986 | European Pat. Off. . |
| 2354 | 2/1964 | France . |
| 4119170 | 12/1992 | Germany . |

OTHER PUBLICATIONS

Cutis (United States), Aug. 1984, vol. 34 No. 2 pp. 190–194, Bicker DR "A comparative study of amcinonide and halcinonide in the treatment of eczematous dermatis".

Cutis, vol. 42, No. 1, 1990, pp. 84–88 The Actiderm Multi–Center Study Group.

The British Journal of Clinical Practice, vol. 20, No. 10, Oct. 1966, David Haler, "An Assessment of Combined Corticosteriods," pp. 511–514.

*Primary Examiner*—Theodore J. Criares
*Attorney, Agent, or Firm*—Hamilton, Brook, Smith & Reynolds, P.C.

[57] ABSTRACT

[A pharmaceutical composition comprises a synergistic combination of about 0.01–0.15% by wt. triamcinolone acetonide and about 0.04–0.3% by wt. halcinonide as active ingredients, in combination with a pharmaceutically acceptable carrier.]

*A pharmaceutical composition comprises a synergistic combination of at least about 0.01% by wt. triamcinolone acetonide and at least about 0.01% by wt. halcinonide as active ingredients therein, in combination with a pharmaceutically acceptable carrier.*

15 Claims, 10 Drawing Sheets

FIG. 1A
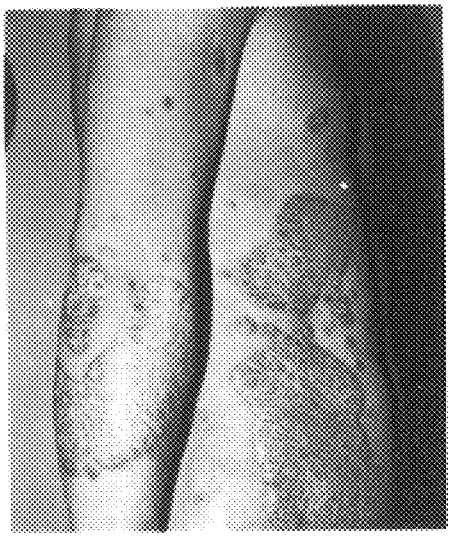
FIG. 1B
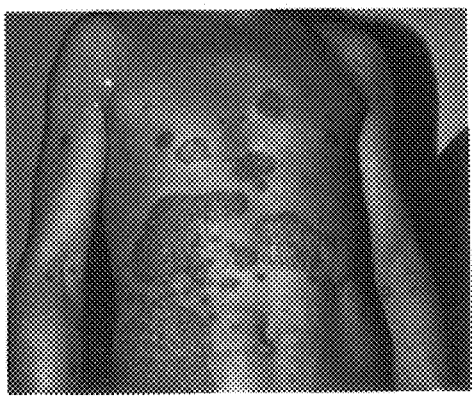
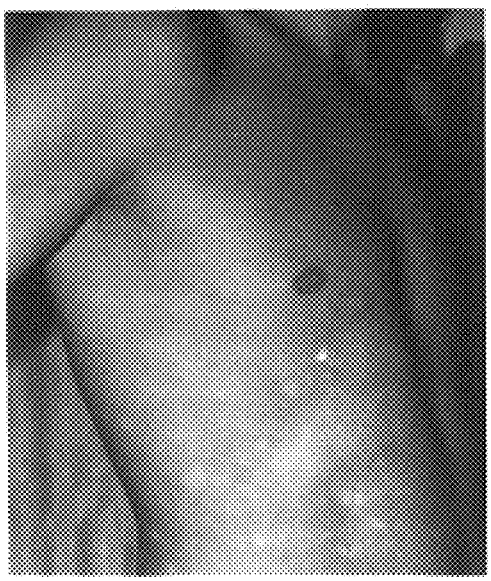
FIG. 1C
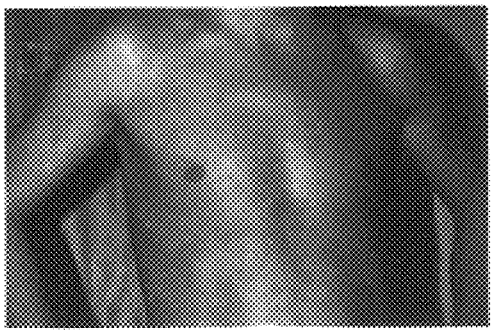
FIG. 1D

FIG. 2A
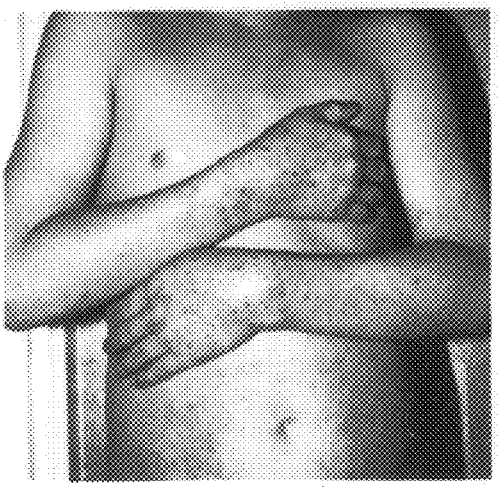
FIG. 2B
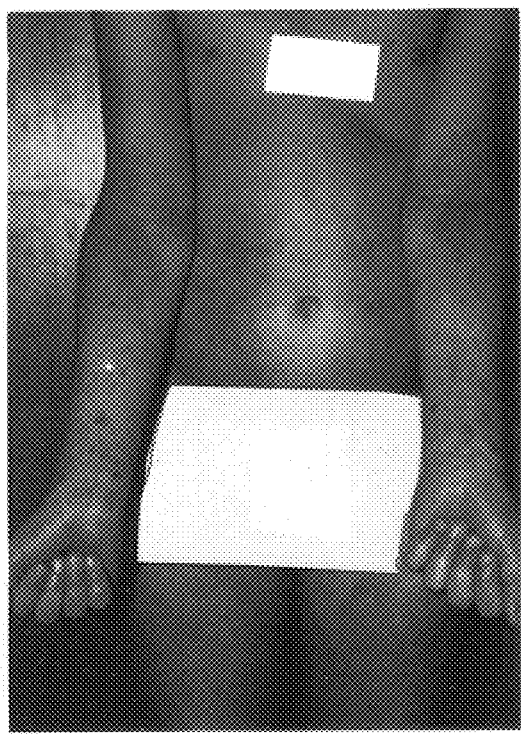
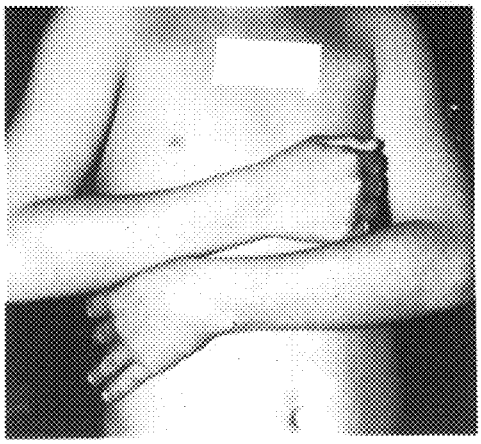
FIG. 2C
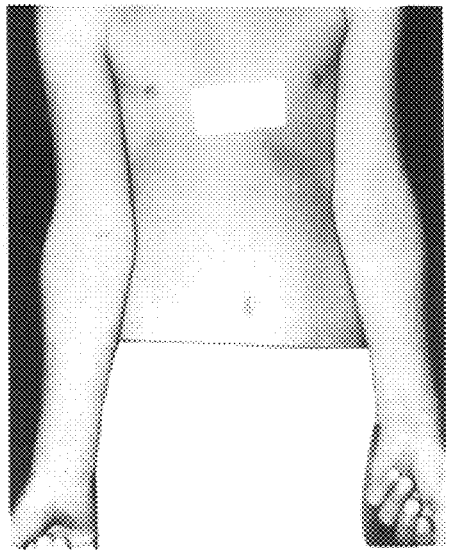
FIG. 2D

FIG.3A
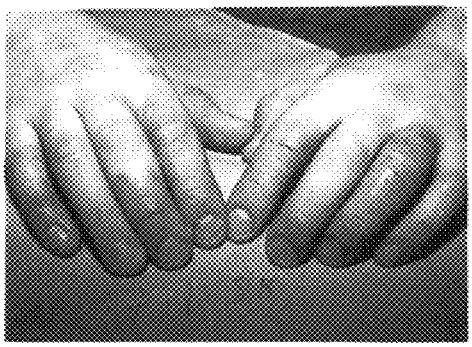
FIG.3B
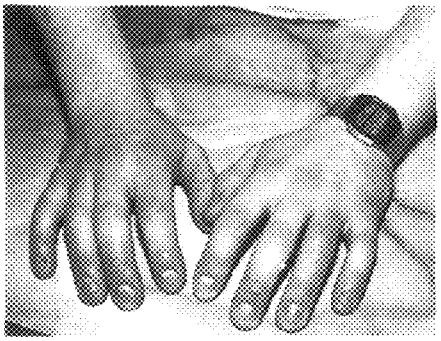
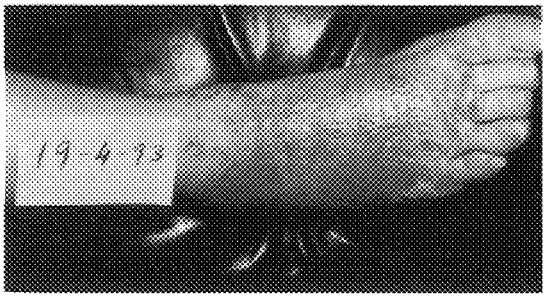
FIG.4A
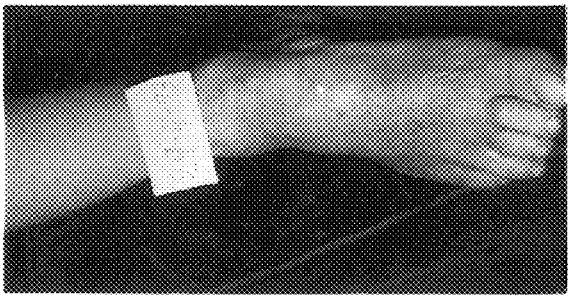
FIG.4B

FIG.5A
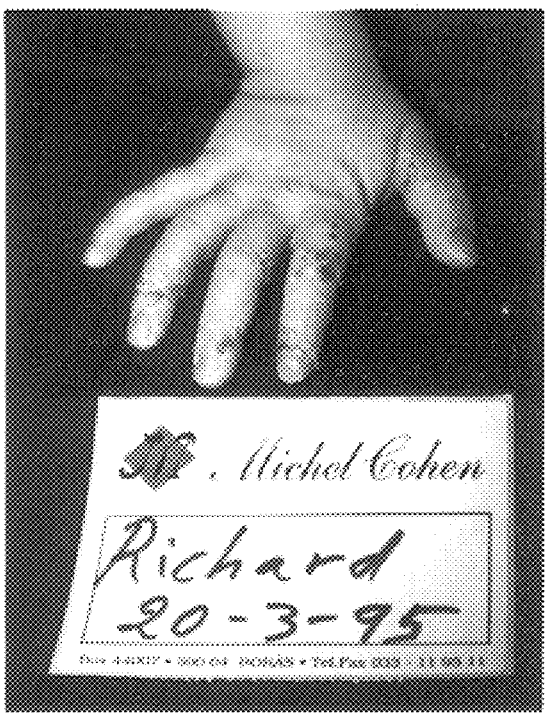
FIG.5B
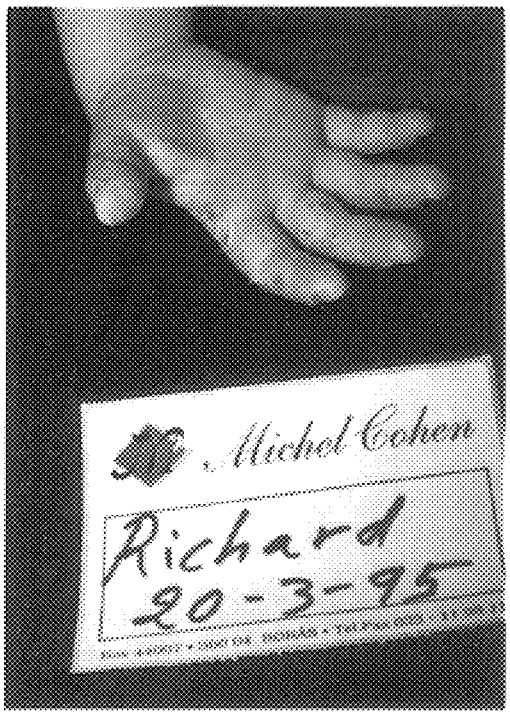
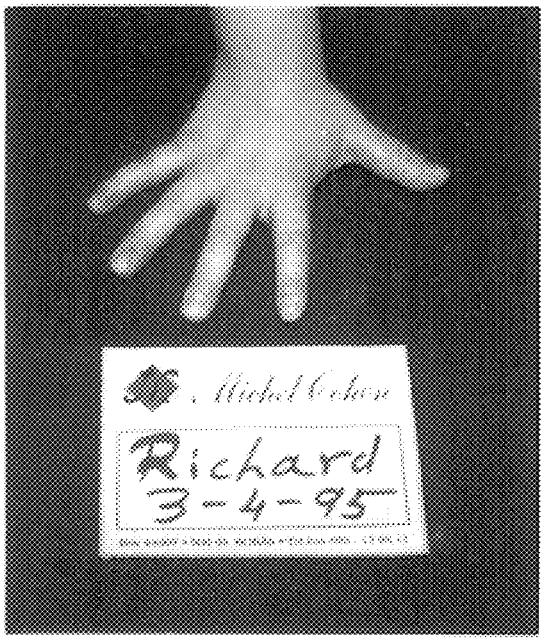
FIG.5C
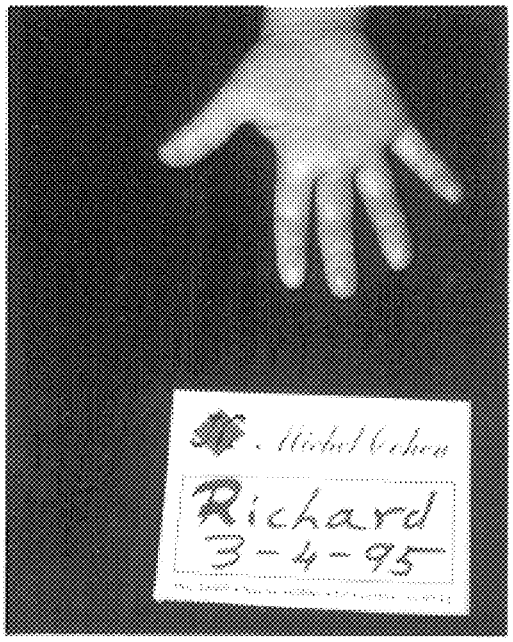
FIG.5D

FIG. 7G
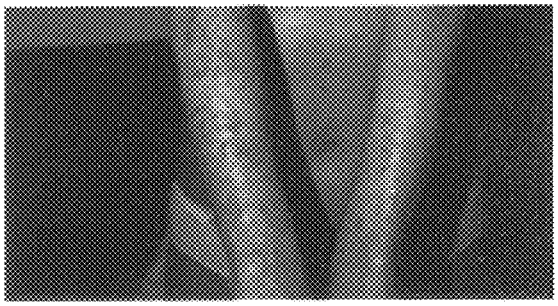
FIG. 7H
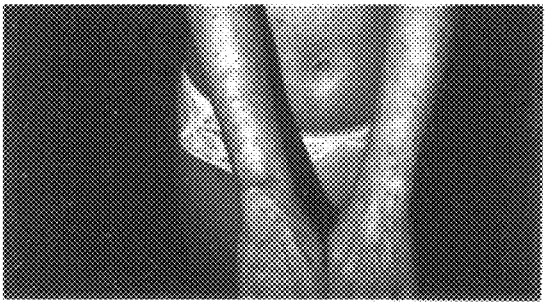
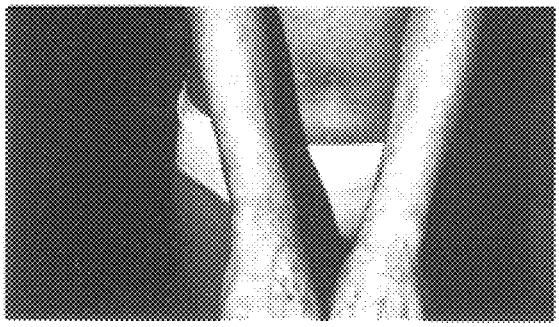
FIG. 7I
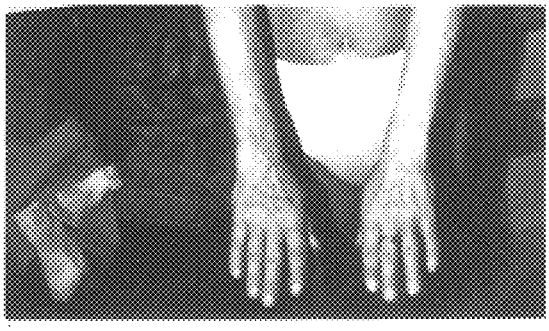
FIG. 7J

FIG.8A
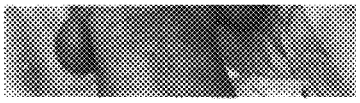
FIG.8B
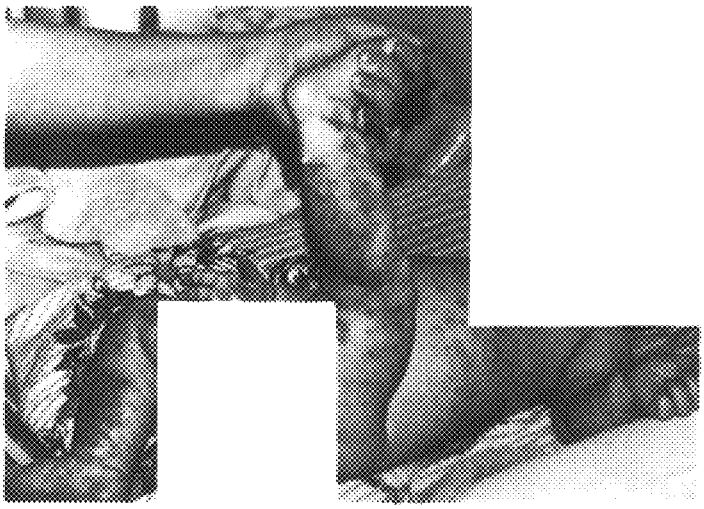
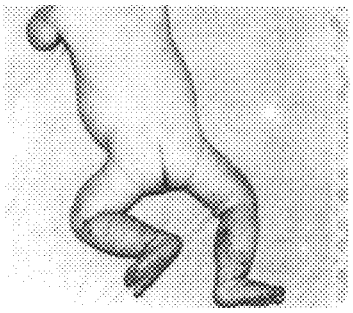
FIG.8C
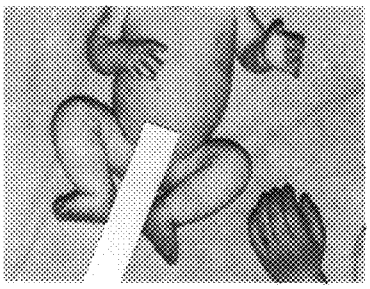
FIG.8D

SYNERGISTIC PHARMACEUTICAL COMPOSITIONS

Matter enclosed in heavy brackets [ ] appears in the original patent but forms no part of this reissue specification; matter printed in italics indicates the additions made by reissue.

[This is a continuation-in-part of application Ser. No. 08/281,642 filed in the United States Patent and Trademark Office on or about Jul. 28, 1994, now abandoned.]

*RELATED APPLICATION*

*This application is a Reissue application of U.S. 08/469,371 filed on Jun. 6, 1995, now U.S. Pat. No. 5,707,981 and is a Continuation-in-part of U.S. Ser. No. 08/281,642, filed Jul. 28, 1994, now abandoned.*

[The present invention relates to a pharmaceutical composition for treating psoriasis. More particularly, the present invention relates to a composition containing 16α, 17α-substituted methylenedioxy steroids as active ingredients therein.]

[It has been known for over 25 years that 11-substituted 16α,17α-substituted methylene dioxysteroids of the pregnane series, as described. e.g.. in U.S. Pat. No. 2,990,401, have high anti-inflammatory activity and can be used topically in the treatment of burns, rheumatoid arthritis, allergies, psoriasis and other skin disorders.]

[Among the compounds taught in said patent, it is now well-known that triamcinolone acetonide, which is 9α-fluoro-11β-21-dihydroxy-16α,17α-isopropylidenedioxy-1,4pregnadiene-3,20-dione, has proved particularly useful in the treatment of dermatological conditions. The compound has been proved to have marked efficacy in the treatment of dermatosis, eczema. neurodermitis, impetigo, psoriasis, pruritis and other related diseases.]

[Similarly in U.S. Pat. No. 3,892,857 there is described and claimed asteroid formulation having enhanced properties for topical application, comprising 21-chloro-9-fluoro-1-hydroxy-16,17-[(1-methyl-ethylidene)bis(oxy)]pregn-4-ene-3,20-dione in a vehicle containing as major ingredients propylene glycol and water.]

[The present invention relates to a pharmaceutical composition for treating psoriasis. More particularly, the present invention relates to a composition containing 16α,17α-substituted methylenedioxy steroids as active ingredients therein.]

[It has been known for over twenty-five years that 11-substituted 16α,17α-substituted methylene dioxysteroids of the pregnane series, as described, e.g., in U.S. Pat. No. 2,990,401, have high anti-inflammatory activity and can be used topically in the treatment of burns, rheumatoid arthritis, allergies, psoriasis and other skin disorders.]

[Among the compounds taught in said patent it is now well known that triamcinolone acetonide, which is 9α-fluoro-11β21-dihydroxy-16α,17α-isopropylidenedioxy-1,4-pregnadiene-3,20-dione, has proved particularly useful in the treatment of dermatological conditions. The compound has been proved to have marked efficacy in the treatment of dermatosis, eczema, neurodermitis, impetigo, psoriasis, pruritis and other related diseases.]

[Similarly, in U.S. Pat. No. 3,892,857 there is described and claimed a steroid formulation having enhanced properties for topical application comprising 21-chloro-9-fluoro-11-hydroxy- 16,17-[(1-methyl-ethylidene)bis(oxy)]pregn-4-ene-3,2-dione in a vehicle containing as major ingredients propylene glycol aid water.]

[Said compound has subsequently become known generally as halcinonide and is marketed as a topical anti-inflammatory compound.]

[While both of said compounds are successfully marketed and are known to ease the suffering caused by psoriasis by stopping the itching, and even cleaning the skin of crust, the basic psoriasis remains uncured.]

*BACKGROUND OF THE INVENTION*

*As described in U.S. Pat. No. 5,171,581 "Psoriasis is a chronic skin disorder that is proliferative in nature and widespread throughout the world, afflicting millions of human and even domesticated animals having similar proliferative integument problems. The skin disorder is characterized by recurrent, elevated red lesions, plaques or rarely, pustules on the skin. These plaques are the result of an excessively rapid growth and shedding of epidermal (skin) cells. No one knows what causes this abnormal cell proliferation. Its severity and course vary greatly from case to case, and also in the individual afflicted with the disease. Recurrences are almost the rule with intervals varying from one month to many years. One person may go through life with a single patch on the elbow, knee or scalp, while another will have repeated attacks of a generalized eruption or widespread chronic lesions lasting for years without remission. As discouraging as it may be, medical science and literature are replete with indications that patients exhibiting such lesions are destined for life to be 'psoriatic.'".*

*Similarly, in a psoriasis fact sheet recently obtained from the National Psoriasis Foundation, it is stated that "Psoriasis affects an estimated 2% of the world's population. Males and females are equally affected, he majority develop initial lesions as young adults. However psoriasis may appear for the first time in infants or the elderly. In psoriasis, skin cells form too quickly and never mature. Cells move to the top of the skin in 3–4 days instead of the normal 28 days. Psoriasis is chronic (it does not go away) and no one has found the cause or a cure."*

*In a fact sheet promulgated by the Eczema Association for Science and Education, eczema is described as "A family of conditions including: atopic dermatitis, contact dermatitis, occupational dermatitis, seborrheic dermatitis, stasis dermatitis and others."*

*In said fact sheet it is also reported that in the United States nearly 15 million people have eczema, a definition which most frequently relates to atopic dermatitis, one of several conditions which fall under the eczema heading 10% of infants in the United States are born with this disease and 60% of those infants retain it in adulthood.*

*It has been known for over 25 years that 11-substituted 16α,17α-substituted methylene dioxysteroids of the pregnane series, as described, e.g., in U.S. Pat. No. 2,990,401, have high anti-inflammatory activity and can be used topically in the treatment of burns, rheumatoid arthritis, allergies, psoriasis and other skin disorders.*

*Among the compounds taught in said patent, it is now well-known that triamcinolone acetonide, which is 9α-fluoro-11β-21-dihydroxy-16α,17α-isopropylidenedioxy-1,4-pregnadiene-3,20-dione, has proved particularly useful in the treatment of dermatological conditions. The compound has been found to have at least some effect in the treatment of dermatosis, eczema, neurodermitis, impetigo, psoriasis, pruritis and other related diseases.*

*Similarly, in U.S. Pat. No. 3,892,857 there is described and claimed a steroid formulation having enhanced properties for topical application, comprising 21-chloro-9-fluoro-11-hydroxy-16,17-[1-methyl-ethylidene)bis(oxy)] pregn-4-ene-3,20-dione in a vehicle containing as major ingredients propylene glycol and water.*

*Said compound has subsequently become known generally as halcinonide and is marketed as a topical anti-inflammatory compound.*

*While both of said compounds are successfully marketed and are known to ease the suffering caused by psoriasis by stopping the itching, and even cleaning the skin of crust, for short periods of time, the basic psoriasis and its outward manifestations do not completely disappear and usually return within weeks of treatment or even during treatment.*

*Thus, e.g., the Bantam Medical Dictionary, 1992, describes psoriasis as follows:*

*"a chronic skin disease in which itchy scaly red patches form on the elbows, forearms, knees, legs, scalp, and other parts of the body. Psoriasis is one of the commonest skin diseases, affecting about 1% of the population, but its cause is not known. The disorder often runs in families and may be brought on by anxiety; it is rare in infants and the elderly the commonest time of onset being in childhood or adolescence. It sometimes occurs in association with arthritis (see psoriatic arthritis). Occasionally the disease may be very severe, affecting much of the skin and causing considerable disability in the patient. There is no known cure and treatment is palliative with lotions or ointments."*

*Thus, as stated at the end of said listing, at present there is no known cure for psoriasis despite the widefelt need therefor.*

*SUMMARY OF THE INVENTION*

*It has now been surprisingly discovered that a combination of said compounds exhibits a synergistic effect which fully or at least temporarily eliminates the sores, scabs, lesions and itching characteristic of psoriasis, eczema, rosacea, dermatitis, and similar related conditions so that after treatment is completed, these conditions do not return at all or return only after several months or years. The present invention relates to a pharmaceutical composition. More specifically, the present invention relates to a synergistic pharmaceutical composition for treating skin disorders such as dermatitis, eczema, psoriasis and associated and related inflammatory conditions. More particularly, the present invention relates to a composition containing 16α, 17α-substituted methylenedioxy steroids as active ingredients.*

*As will be described and exemplified hereinafter with regard to Example 2, it has now been surprisingly found and proven that a combination of as little as 0.01% halcinonide and 0.01% triamcinolone acetonide is more effective in the treatment of severe psoriasis than 0.3% halcinonide or 0.3% triamcinolone acetonide when administered separately. While said combination does not remove all the spots associated with severe psoriasis, it is effective for treating mild psoriasis, eczema and dermatitis as well as other dermatological conditions and even lower dosages of the newly discovered synergistic combination of the present invention should be effective for treating milder dermatological conditions involving dry and/or itchy skin.*

[DESCRIPTION OF DRAWINGS]

[FIG. 1A through 8D illustrate the synergistic effect of the composition of Examples 1–3.]

*BRIEF DESCRIPTION OF THE DRAWINGS*

Figure 6A:
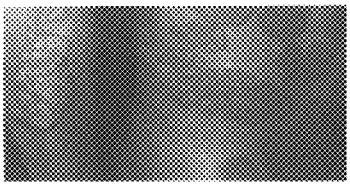

*FIGS. 1A, 1B, 1C, 1D, 2A, 2B, 2C, 2D, 3A, 3B, 3C, 4A, 4B, 5A, 5B, 5C, 5D, 6A, 6B, 6C, 6D, 6E, 6F, 7A, 7B, 7C, 7D, 7E, 7F, 7G, 7H, 7I, 7J, 8A, 8B, 8C, and 8D are photographs of patients before and after treatment with a composition according to the invention and, in some instances, treated with control compositions.*

[It has now been surprisingly discovered that a combination of said compounds exhibits a synergistic effect which not only heals psoriasis but also cures said condition, so that even after treatment is completed, the psoriasis does not return.]

[The present invention provides a pharmaceutical composition comprising a synergistic combination of about 0.01–0.15% by wt. triamcinolone acetonide and about 0.00–0.3% by wt. halcinonide as active ingredients therein, in combination with a pharmaceutically acceptable carrier.]

[Preferably, according to the present invention, there is provided a pharmaceutical composition for treating psoriasis, comprising a synergistic combination of about 0.05–0.15% by wt. triamcinolone acetonide and about 0.2–0.3% by wt. halcinonide as active ingredients therein, in combination with a pharmaceutically acceptable carriers.]

[Said composition preferably comprises a pharmaceutical composition comprising about 0.1% triamcinolone acetonide and about 0.2% halcinonide. The pharmaceutically acceptable carrier can be any of those known and taught in the prior art.]

[The formulation of this invention may also contain additives to improve the physical form and the release characteristics. Additives which may be used include diluents, thickness agents, preservatives and penetration enhancers.]

[The penetration enhancers suitable for the purpose of the invention are the therapeutically acceptable penetration enhancers that do not adversely affect the drug, the skin or the materials for using the ointment.]

[Examples of penetration enhancers include 1-dodecylazacydoheptan-2-one, propylene glycol, surfactants and others.]

[Thus it will be understood that the present invention also provides a pharmaceutical composition for treating psoriasis comprising a synergistic combination of about 0.01–0.15% by wt. triamcinolone acetonide and about 0.04–0.3% by wt. halcinonide as active ingredient therein when said active ingredient are used in combination with a penetration enhancer.]

[A preferred formulation comprises a base of about 70% vaselin albun, 10% lanoline and 20% lanet wax and 325 ml water to form about 1 kilogram of ointment cream carrier for said active ingredients.]

[While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the inventions.]

[EXAMPLE 1]

[Two compositions according to the present invention were prepared in the following manner:

[Preparation of the Base]

[Vaseline (70%) was mixed with lanolin (20%) and lanet wax (10%) was added while heating at a temperature not exceeding 70° C. and mixing constantly in order to maximize the homogenicity of the base, 30% water was added at 70° C.]

[Active Ingredients]

[1 1a) Per 100 g ointment—200 mg haleinonide 100 mg triamcinolene]

[1 1b) Forte. per 100 g ointment—300 mg haleinonide 100 mg triamcinolone]

[The above amounts of active ingredients were respectively mixed together with a mortar and pestle with the held of a drop of parafin. While mixing constantly the base was added drop by drop at first, then more rapidly, until a total amount of 100 gm was obtained.]

[COMPARATIVE EXAMPLE 2]

[1 a) A comparative composition was prepared as in example 1, however having only 0.1% halcinonide and 0.1% triamcinolone actamide in the final composition.]

[1 b) A comparative composition was prepared as in Example 1, having 0.3% halcinonide.]

[1 c) A comparative composition was prepared as in Example 1 having 0.3% triamcinolone acetonide.]

[A volunteer patient having severe psoriasis over the entire body was treated at different sites with compositions 1a, 1b and comparative compositions 2a, 2b and 2c.]

[The observed results were as follows:]

[1 Composition 2a—Some spots of the psoriasis disappeared, but not all and where they did fade, pink color remained.]

[1 Composition 2b—No results—no improvement. ]

[1 Composition 2c—No results—no improvement. ]

[1 Composition 1a—Within one week of treatment the psoriasis on the entire area of treatment disappeared with skin returning to normal color except for a few isolated spots of original long established psoriasis. (These spots also disappeared upon treatment with composition 1b).]

[1 Composition 1b—within one week of treatment the spots completely disappeared with skin returning to normal color and with no sign of previous psoriasis.]

[It should be noted that this experiment was performed on a subject with a serious case of psoriasis covering parts of the entire body and that while the prior art formulations in their maximum permitted dose had no appreciable effect, the compositions of the present invention effected a complete cured.]

[EXAMPLE 3]

[Several volunteer patients suffering from psoriasis were treated with composition 1a as prepared in Example 1. The treatment was as follows.]

[Composition is applied twice a day for two weeks, morning and evening. A very small amount is used each time, massaged very well into the skin. If the psoriasis disappeared by the end of these two weeks, the patient continued use once a day for three weeks. If psoriasis did not completely disappear patient was given composition 1b and treatment given two times a day for two weeks and then once per day for three weeks.]]

[The following results were observed:]

[Total success of the above treatments was achieved in 70% of the cases in which the psoriasis disappeared completely and did not return for the two year observation period. In the remaining 30%, there was marked improvement but when treatment was stopped the psoriasis returned.]

[It is to be noted that on the one hand a combination of 0.1% halcinonide and 0.1% triamcinolone acetonide is insufficient to effect a cure of psoriasis, and on the other hand, combined amounts of active ingredients above 0.4% are inadvisable because they repress adrenaline. Combinations within that range, however, provided that the amount of halcinonide is greater than the amount of triamcinolone acetonide, are effective and contemplated for use according to the present invention.]

[It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the fore-going description, and all changes which come within the meaning and range of equivalency of the claims are therefore intended to be embraced therein.]

*DETAILED DESCRIPTION OF THE INVENTION*

*Thus, the present invention provides a pharmaceutical composition comprising a synergistic combination of at least about 0.01% by wt. triamcinolone acetonide and at least about 0.01% by wt. halcinonide as active ingredients therein, in combination with a pharmaceutically acceptable carrier.*

*While said lower range of components has been tested and found to exhibit the above described synergism, it is believed that it is within the routine skill of the art to determine the minimum synergistic combination to apply to various degrees of various conditions, taking into account age, severity, particular conditions, body weight location of the condition on the patient's body etc., and therefore all effective ranges of the novel synergistic composition of the present invention are contemplated as being provided herein.*

*Thus it has now been surprisingly discovered that the synergistic composition of the present invention can be effectively used for the treatment of various dermatological diseases such as for instance contact dermatitis and related allergies, eczema of physical, chemical and medical origin, flexural and housewive's eczema, impetigo, psoriasis, erythema, rosacea, nickle allergies, cradle cap in infants, neurodermititis, pruritis, dry skin and other related diseases and conditions.*

*It has further been found that due to the anti-inflammatory effects of the synergistic composition of the present invention and the penetration of the topical composition of the present invention through the skin, relief of arthritic pain associated with psoriasis and of other inflammatory conditions is also obtained.*

*In preferred embodiments of the present invention there is provided a pharmaceutical composition comprising a syn-*

*ergistic combination of at least about 0.01–0.3% by wt. triamcinolone acetonide and at least about 0.01–0.3% by wt. halcinonide as active ingredients therein, in combination with a pharmaceutically acceptable carrier.*

*With regard to the upper range of the combined components of the synergistic composition of the present invention, it is to be noted that combined amounts of active ingredients above between about 0.4 and 0.6% are inadvisable because they may repress adrenaline and thus possible negative side effects may be a limiting factor on the upper range which should be used according to the present invention. Taking the above into account, all combinations within the ranges set forth herein are effective and contemplated for use according to the present invention.*

*The term "pharmaceutically acceptable carrier", as used herein, is intended to denote any of the formulations standardly used for topical application, i.e. cream, ointment, lotion, gel or the like, as is known per se in the art and as described, e.g. for similar compositions in U.S. Pat. No. 3,934,013, the description of which is incorporated herein by reference.*

*Thus, according to the present invention, there is provided a pharmaceutical composition for treating psoriasis, comprising a synergistic combination of about 0.01–0.3% by wt. triamcinolone acetonide and about 0.01–0.3% by wt. halcinonide as active ingredients therein, in combination with a pharmaceutically acceptable carrier.*

*The invention also provides a pharmaceutical composition for treating eczema, comprising a synergistic combination of about 0.01–0.3% by wt. triamcinolone, acetonide and about 0.01–0.3% by wt. halcinonide as active ingredients therein, in combination with a pharmaceutically acceptable carrier.*

*Also provided according to the present invention is a pharmaceutical composition for treating dermatitis comprising a synergistic combination of about 0.01–0.3% by wt. triamcinolone acetonide and about 0.01–0.3% by wt. halcinonide as active ingredients therein, in combination with a pharmaceutically acceptable carrier.*

*Said compositions preferably comprise about 0.1% triamcinolone acetonide and about 0.1% halcinonide, which combination removes the external manifestations of the above conditions and which combination has been found to be safe in tests carried out in over 1600 volunteer patients.*

*Furthermore, said preferred dosage has been found to successfully bring about extended remission of the external manifestations in even the most severe cases, as can be seen, e.g., with reference to the accompanying figures which include photographs of patients who had suffered for many years despite treatment with different cortisone and other active ingredients without success.*

*More recently, tests have been carried out in hundreds of patients with compositions according, to the present invention comprising about 0.02% triamcinolone acetonide and about 0.02% halcinonide, and as illustrated hereinafter in comparative Example 4, and with reference to FIGS. 6A–6F treatment with said reduced dosages even in severe cases appears to provide relief similar to that provided by the compositions containing about 0.1% triamcinolone acetonide and about 0.1% halcinonide.*

*The pharmaceutically acceptable carrier can be any of those known and taught in the prior art.*

*The formulation of this invention may also contain additives to improve the physical form and the release characteristics. Additives which may be used include diluents, thickening agents, preservatives and penetration enhancers.*

*The penetration enhancers suitable for the purpose of the invention are the therapeutically acceptable penetration enhancers that do not adversely affect the drug, the skin or the materials for using the ointment.*

*Examples of penetration enhancers include 1-dodecylazacycloheptan-2-one, propylene glycol, surfactants and others.*

*A preferred formulation comprises a base of about 450–500 g petroleum jelly sold under the trademark Vaseline®, about 65–75 g lanoline and about 120–150 g lanet wax combined together and then mixed with about 300–350 ml water to form about 1 kilogram of ointment cream carrier for said active ingredients.*

*While the invention will now be described in connection with certain preferred embodiments in the following examples and with reference to the accompanying Figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.*

*FIGS. 1A and 1B are photographs taken of a patient suffering from severe psoriasis, before treatment with a composition according to the present invention;*

*FIGS. 1C and 1D are photographs taken of the same patient three months after treatment.*

*FIGS. 2A and 2B are photographs take of a patient suffering from allergic eczema before treatment with a composition according to the present invention;*

*FIGS. 2C and 2D are photographs taken of the same patient three weeks after treatment.*

*FIGS. 3A and 3B are photographs taken of a patient suffering from atopic eczema before treatment with a composition according to the present invention and two weeks after treatment.*

*FIGS. 4A and 4B are photographs taken of a patient suffering from severe dermatitis of the foot before treatment with a composition according to the present invention, and ten days after treatment respectively.*

*FIGS. 5A and 5B are photographs taken of a patient suffering from severe eczema of the hand before treatment with a composition according to the present invention.*

*FIGS. 5C and 5D are photographs taken of the same patient two weeks after treatment.*

Figure 6B:
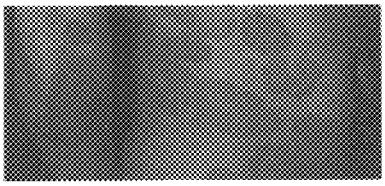
Figure 6C:
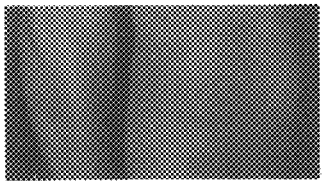

*FIGS. 6A, 6B and 6C, are photographs taken of a patient suffering from severe psoriasis before treatment, 1 week into treatment, and 3 weeks after treatment with a composition containing a total of 0.2% active ingredients applied to one side of his body, according to the present invention.*

Figure 6D:
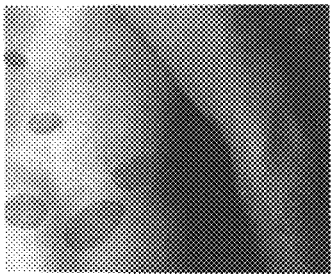
Figure 6E:
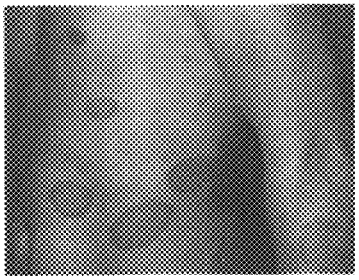
Figure 6F:
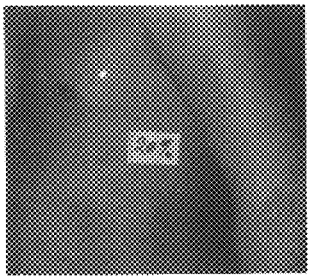

*FIGS. 6D, 6E and 6F are photographs taken of the same patient of FIGS. 6A, 6B and 6C before treatment, 1 week into treatment, and 3 weeks after treatment with a composition containing a total of 0.04% active ingredients applied to the other side of his body, according to the present invention.*

Figure 7A:
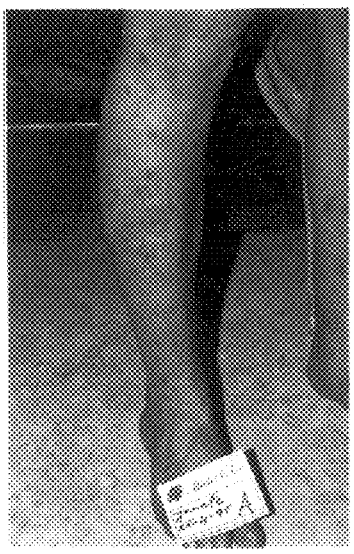
Figure 7B:
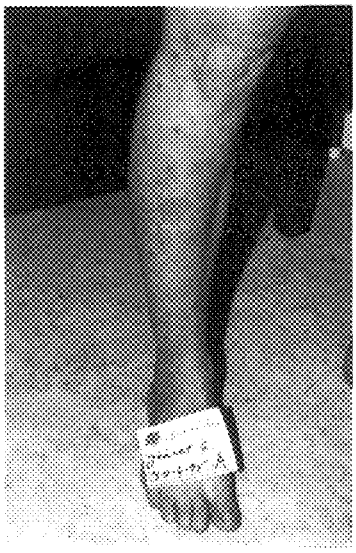
Figure 7C:
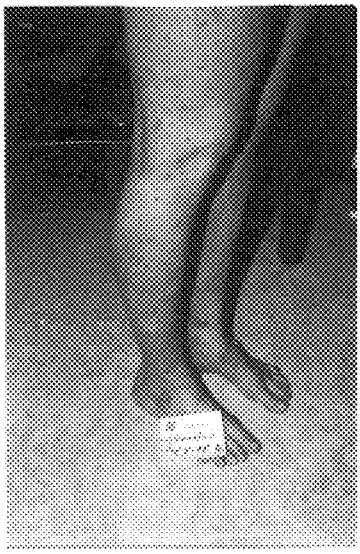

*FIGS. 7A, 7B and 7C are photographs taken of the right leg of a patient suffering from eczema taken before*

*treatment, 1 week into treatment and 3 weeks into treatment with a comparative composition containing 0.2% tiamcinolone acetonide as the sole active ingredient.*

Figure 7D:
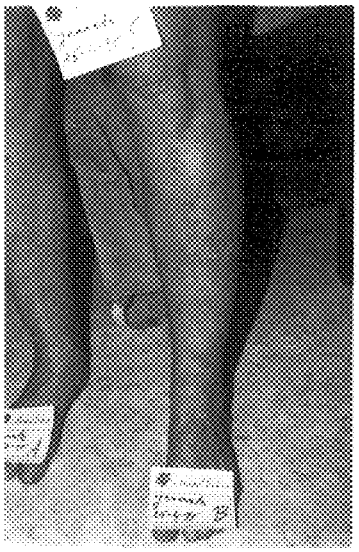
Figure 7E:
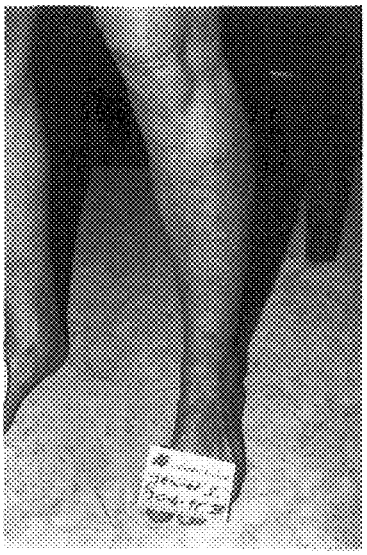
Figure 7F:
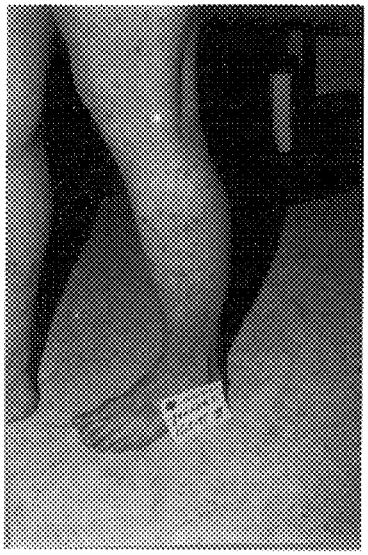

*FIGS. 7D, 7D, and 7F are photographs taken of the left leg of a patient suffering from eczema taken before treatment, 1 week into treatment, 3 weeks into treatment and 4 weeks into treatment with a composition according to the present invention containing 0.1% halcinonide and 0.1% triamcinolone acetonide as combined active ingredients therein.*

*FIGS. 8A and 8B are photographs of an infant suffering from infant dermatitis before treatment; and*

*FIGS. 8C and 8D are pictures of the same infant taken 2 months later after treatment with a composition according to the present invention.*

*In the following examples and referring to FIGS. 1A–8D, compositions according to the present invention containing 0.1% halcinonide and 0.1% triamcinolone acetonide were used except where otherwise indicated.*

*EXAMPLE 1*

*Two compositions according, to the present invention were prepared in the following manner:*

*Preparation of the Base*

*Vaseline® (490 g) was mixed with lanolin (70 g) and lanet wax (140 g) was added while heating at a temperature not exceeding 70° C. and mixing constantly in order to maximize the homogenicity of the base. 300 g water was added at 70° C.*

*Active Ingredients*

*1a) Per 100 g ointment—200 mg halcinonide —100 mg triamcinolone*

*1b) Per 100 g ointment—300 mg halcinonide —100 mg triamcinolone (Forte-extra strength formulation)*

*The above amounts of active ingredients were respectively mixed together with a mortar and pestle with the help of a drop of paraffin. While mixing constantly the base was added drop by drop at first, then more rapidly, until a total amount of 100 gm was obtained.*

*COMPARATIVE EXAMPLE 2*

*a) A comparative composition was prepared as in Example 1, however having only 0.01% halcinonide and 0.01% triamcinolone acetonide in the final composition.*

*b) A comparative composition was prepared as in Example 1, having 0.3% halcinonide as sole active ingredient.*

*c) A comparative composition was prepared as in Example 1, having 0.3% triamcinolone acetonide as sole active ingredient.*

*A volunteer patient having severe psoriasis over the entire body was treated at different sites with compositions 1a, 1b and comparative compositions 2a, 2b and 2c by application of minor equal amounts massaged into effected areas twice a day for a three week period.*

*The observed results were as follows:*

*Composition 2a—Some spots of the psoriasis disappeared, but not all, and where they did fade, pink color remained.*

*Composition 2b—No lasting results—no appreciable improvement.*

*Composition 2c—No lasting results—no appreciable improvement.*

*Composition 1a—Within one week of treatment the psoriasis on the entire area of treatment disappeared with skin returning to normal color except for a few isolated spots of original long established psoriasis. (These spots also disappeared upon treatment with composition 1b)*

*Composition 1b—Within one week of treatment the spots completely disappeared with skin returning to normal color and with no sign of previous psoriasis.*

*It should be noted that this experiment was performed on a subject with a severe case of psoriasis covering parts of the entire body and that while the prior art formulations in their maximum permitted dose had no appreciable effect, the compositions of the present invention effected a complete removal of all external manifestations of the psoriasis which lasted for over a one year period before the recurrence of the condition.*

*EXAMPLE 3*

*Over 1600 volunteer patients suffering from psoriasis, atopic eczema, allergic eczema, rosacea, and other similar dermatological conditions were treated with compositions according to the present invention.*

*The patients were instructed to apply the composition twice a day for a period of between 2 and 4 weeks, morning and evening until all external manifestations disappeared, and then the composition was applied once a day for an additional period of 1 week. A very small amount was used each time, massaged very well into the skin.*

*In this extended testing it was found with regard to psoriasis patients that approximately 5% had no recurrence even after eight years approximately 40% had no recurrence for a period in excess of twelve months and another approximately 40% had no recurrence for a period in excess of six months. In those volunteers in which a recurrence was noted, application of the composition according to the present invention once again affected a removal of all external manifestations for an extended period of time.*

*Among the sixteen hundred volunteers tested were people suffering from psoriasis, eczema of different types, causes and severity as well as people suffering from rosacea, and dermatitis of different types, causes and severity.*

*While not sufficiently tested under controlled conditions, it has been reported by volunteer patients that the composition of the present invention was also effective in treating sores associated with herpes simplex, pain associated with arthritis, even when said arthritis was not associated with psoriasis and bursitis.*

*Referring to FIGS. 1A and 1B, there is seen a volunteer patient who reported having had suffered from severe psoriasis for over twenty years with extensive lesions on his chest, stomach and arms.*

*After three weeks of treatment with the composition of the present invention, the lesions had disappeared. The patient returned and was photographed after three months and the results are seen in FIGS. 1C and 1D. As illustrated, only minor discolorations and scaring from the original severe psoriasis appear, while the skin is totally clear of active sores and lesions.*

*Referring to FIGS. 2A and 2B, there is seen a young boy who is allergic to eggs, citrus fruits, chocolate, nuts, fish, tomatoes, ketchup, strawberries and other food products which all give him allergic eczema, from which he has suffered all his life. As illustrated in these pictures, the boy's arms and stomach are covered with eczema spots and sores.*

*This volunteer patient was treated with a composition of the present invention and his mother reported that after for days 80% of his rash had disappeared, as had the accompanying itching feeling. After ten days the entire rash was gone.*

*FIGS. 2C and 2D are photographs taken 2½ weeks after commencement of treatment and, as can be seen, the skin is completely clear of all rash and sores.*

*FIG. 3A is a photograph of the hands of a dishwasher, suffering from atopic eczema, whose fingers were swollen and chapped and even infected. He had used cortisone creams over a period of over five years, ranging in prescriptions of 1% to 3% without relief. After two weeks of treatment with the composition of the present invention, the swelling, infection and chapping had all disappeared as shown in FIG. 3B.*

*FIG. 4A is a photograph of the foot of a volunteer patient suffering from dermatitis. As can be seen, his foot is dry and scaly with scabs and sores. FIG. 4B is a photograph of the same patient taken only ten days later, after treatment with a composition of the present invention. As can be seen, the foot exhibits a marked improvement, being free of scales, scabs and sores and having returned to almost a normal color, which was achieved after an additional one week of treatment with the composition of the present invention.*

*FIGS. 5A and 5B are photographs of a 4½ year old boy suffering from severe eczema of the hands. As can be seen his hands and tips of the fingers are covered with scales, sores, scabs and white lesions, and patches are even hanging from his finger tips. His mother advised that he had suffered from this condition all his life, and that treatment with cortisone and other recommended creams did not remove this condition.*

*After 2 weeks of treatment with a composition of the present invention the hands are completely free and clean of all sores and scabs, as can be seen in FIGS. 5C and 5D.*

*COMPARATIVE EXAMPLE 4*

*The same patient who suffered severe psoriasis and was treated in 1988 as discussed with reference to FIGS. 1A–1D, suffered a recurrence of the condition and agreed to try two different formulations of compositions according to the present invention on the two sides of his body.*

*As indicated hereinbefore, FIGS. 6A, 6B and 6C are photographs taken before treatment, 1 week into treatment, and 3 weeks after treatment with a composition containing a total of 0.2% active ingredients applied to one side of the body, while FIGS. 6D, 6E and 6F are photographs taken of the same patient of FIGS. 6A, 6B and 6C before treatment, 1 week into treatment, and 3 weeks after treatment with a composition containing a total of 0.04% active ingredients applied to the other side of the body.*

*As will be noted from FIGS. 6A and 6D, on Apr. 28, 1995, both sides of the body and both arms exhibited large patches of encrusted lesions. As can be seen from FIGS. 6B and 6E, already on May 1, 1995, a major improvement is noted wherein the encrusted lesions have disappeared and there remain only milder red patches. Referring now to FIGS. 6C and 6F, 3½ weeks after treatment, even the red patches have disappeared leaving only mild discolorations, both on the side treated with a diluted composition containing only 0.02% triamcinolone acetonide and 0.02% halcinonide, As can be seen, there is no appreciable difference to the visible eye between the effect of these compositions of different dosages according to the present invention.*

*COMPARATIVE EXAMPLE 5*

*A further comparative test was carried out on a patient suffering from eczema on extensive parts of her body. This patient was instructed to apply three creams to different parts of her body without being told the content of the various creams. The first cream contained 0.2% triamcinolone acetonide, and was applied to the right leg with the results being shown in FIGS. 7A, 7B and 7C. The second cream contained 0.2% halcinonide and was applied to the left leg with the results being shown in FIGS. 7D, 7E and 7F. The third cream contained a combination of 0.1% triamcinolone acetonide and 0.1% halcinonide and was applied to the arms with the results being shown in FIGS. 7G, 7H, 7I and 7J.*

*The volunteer patient reported having severe atopic eczema since birth, having used cortisone creams over long periods for the last 36 years, without relief from the rash and itching which accompany this condition.*

*Referring to FIGS. 7A, 7D and 7G, the itchy scabby sores on the arms and legs of the patient are quite evident. Referring to FIGS. 7B, 7E and 7H, it can he noted that one week after treatment the sores still remain, however are much milder.*

*The major difference between the three creams becomes evident however, three weeks into treatment, wherein the sores are almost completely gone on the arms of the patient, as can be seen from FIG. 7I, however, have returned and begun to be even worse on both legs of the patient, as seen in FIGS. 7C and 7F when compared to FIGS. 7B and 7E.*

*The patient also reported that in all areas that were treated with cream c, the skin had become better and better, but in the areas that were treated with a and b, the rash began to return and was resistant to the treatment and small open sores reformed on the skin.*

*At this point and time, the patient refused to continue using creams a and b, and switched to the use of cream c (which is the cream according to the present invention), on all parts of her body.*

*FIG. 7J shows the arms of the patient clear of all sores after less than one month of treatment and the patient reported that the rash is completely gone, the sores are completely gone, and the skin is continuing to improve and be softer and more supple every day.*

*Referring now to FIGS. 8A and 8B there are seen photographs of an infant suffering from severe infant dermatitis before treatment and having extensive red rash areas on both the front and back of his body.*

*FIGS. 8C and 8D are pictures of the same infant taken 2 months later after treatment with a composition according to the present invention, and as can be seen, the body is almost completely clear of the original rash.*

*While this invention has been particularly shown and described with references to preferred embodiments thereof, it will be understood by those skilled in the art that various changes in form and details may be made therein without departing from the spirit and scope of the invention as defined by the appended claims.*

What is claimed is:

1. A pharmaceutical composition comprising triamcinolone acetonide and halcinonide in synergistic and effective amounts in combination with a pharmaceutically acceptable carrier.

2. A pharmaceutical composition comprising about 0.1% triamcinolone acetonide and about 0.1% halcinonide in combination with a pharmaceutical carrier.

3. A pharmaceutical composition according to claim 1, wherein said pharmaceutically acceptable carrier is a topical cream.

4. A pharmaceutical composition comprising triamcinolone acetonide and halcinonide in synergistic and effective amounts in combination with one or more of petroleum jelly, lanoline, and lanet wax.

5. A pharmaceutical composition of claim 4, further comprising water.

6. A pharmaceutical composition comprising about 0.1% triamcinolone acetonide, about 0.1% halcinonide, about 45 to 50% vaseline, about 6.5 to 7.5% lanoline, about 12 to 15% lanet wax, and a remainder of water, wherein, the percent values are characterized by weight.

7. A method for treating psoriasis in a patient comprising topically administering a composition of claim 1.

8. A method for treating psoriasis in a patient comprising topically administering a composition of claim 4.

9. A method for treating psoriasis in a patient comprising topically administering a composition of claim 6.

10. A method for treating dermatitis in a patient comprising topically administering a composition of claim 1.

11. A method for treating dermatitis in a patient comprising topically administering a composition of claim 4.

12. A method for treating dermatitis in a patient comprising topically administering a composition of claim 6.

13. A method for treating eczema in a patient comprising topically administering a composition of claim 1.

14. A method for treating eczema in a patient comprising topically administering a composition of claim 4.

15. A method for treating eczema in a patient comprising topically administering a composition of claim 6.

* * * * *